(12) United States Patent
Bornzin et al.

(10) Patent No.: US 9,623,235 B1
(45) Date of Patent: Apr. 18, 2017

(54) LEFT VENTRICULAR LEAD WITH ACTIVE FIXATION

(71) Applicant: PACESETTER, INC., Sylmar, CA (US)

(72) Inventors: Gene A. Bornzin, Simi Valley, CA (US); Zoltan Somogyi, Simi Valley, CA (US); Didier Theret, Porter Ranch, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 14/877,728

(22) Filed: Oct. 7, 2015

(51) Int. Cl.
*A61N 1/05* (2006.01)
*A61N 1/372* (2006.01)

(52) U.S. Cl.
CPC .... *A61N 1/0573* (2013.01); *A61N 2001/0585* (2013.01)

(58) Field of Classification Search
None
See application file for complete search history.

(56) References Cited

U.S. PATENT DOCUMENTS

| | | | |
|---|---|---|---|
| 6,253,111 B1* | 6/2001 | Carner | A61N 1/056 600/373 |
| 7,532,939 B2* | 5/2009 | Sommer | A61N 1/0575 607/127 |
| 7,657,325 B2* | 2/2010 | Williams | A61N 1/0573 607/115 |
| 8,029,470 B2* | 10/2011 | Whiting | A61M 25/0041 604/164.01 |

* cited by examiner

*Primary Examiner* — Brian T Gedeon

(57) ABSTRACT

Disclosed herein is a left ventricular lead for tracking over a guide wire into a coronary sinus and providing active fixation in, or adjacent to, the coronary sinus. The guide wire is configured for coronary sinus lead implantation and has an outer diameter. In one embodiment, the lead includes a tubular body including a proximal end, a distal end and a central lumen through which the guide wire is extendable. The lead also includes a lead connector end proximally projecting from the proximal end and comprising at least one electrical contact. The lead also includes a fixed helical anchor comprising a wire member having a diameter of between approximately 0.22 mm and approximately 0.27 mm. The wire member distally extends away from the distal end in a helical arrangement including an inner helical coil diameter that is sufficient to allow the guide wire to extend through the fixed helical anchor.

20 Claims, 5 Drawing Sheets

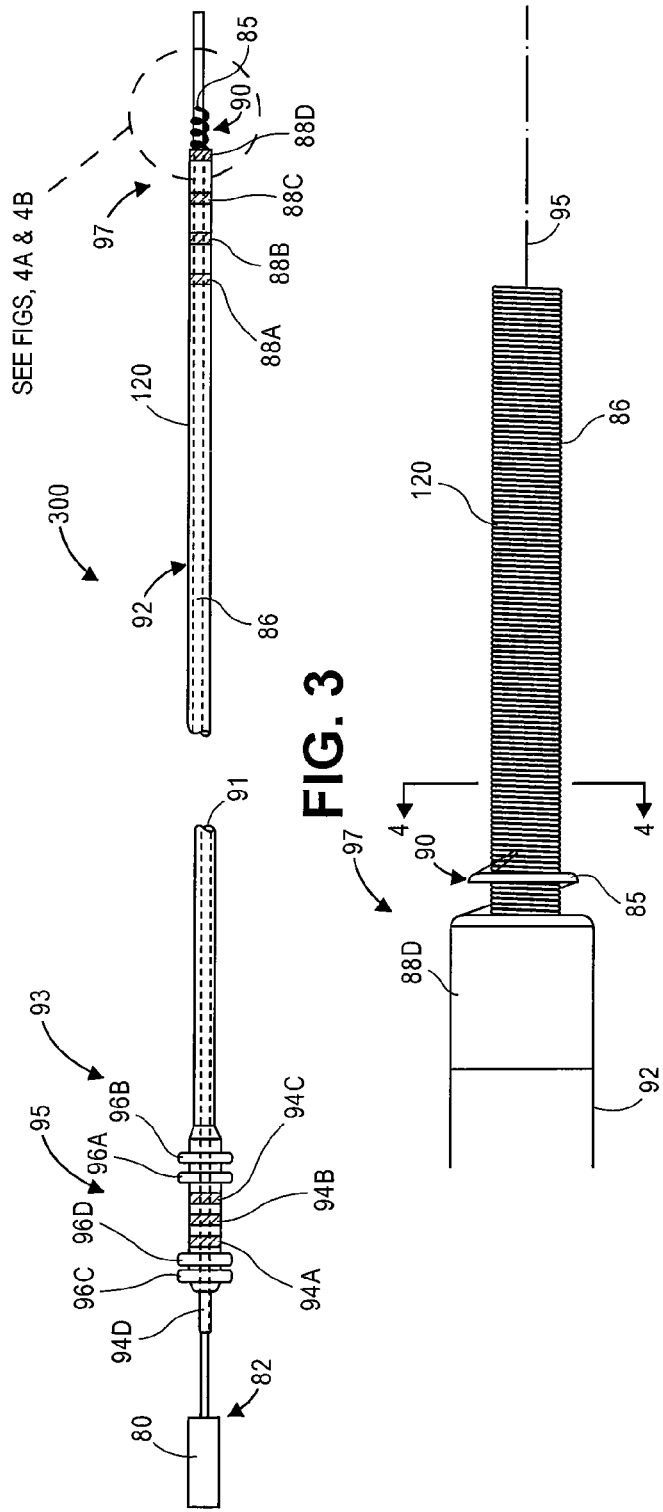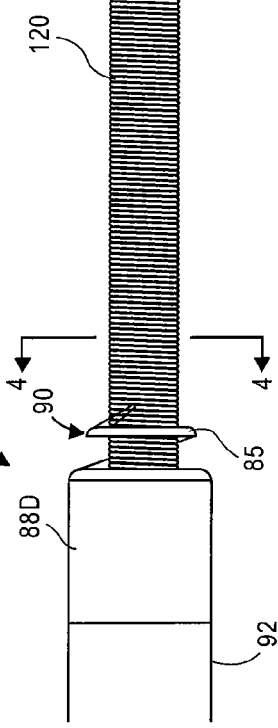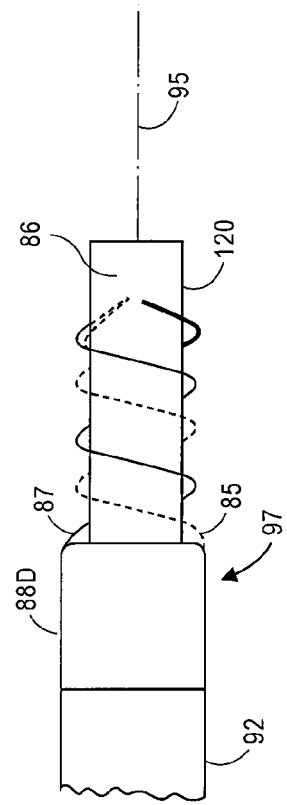

LEFT VENTRICULAR LEAD WITH ACTIVE FIXATION

FIELD OF THE INVENTION

Aspects of the present invention relate to medical apparatus and methods. More specifically, the present disclosure relates to implantable left ventricular leads and methods of using such leads.

BACKGROUND OF THE INVENTION

Implantable cardiac pulse generators (e.g., pacemakers, implantable cardioverter defibrillators (ICD), or etc.) often include elongated medical electrical leads that can be advanced into patient hearts. The electrical leads include electrodes to sense electrical activity and deliver therapeutic stimulation. In recent years, left ventricular (LV) leads are advanced into the coronary sinus in order to position the electrodes of the leads at left ventricular pacing sites, typically located in proximity to the base of the left ventricle.

Some patients may have very small subclavian veins and may require leads smaller than 6 F or 5 F to transverse the small subclavian veins. Some patients may have complex venous anatomies that are difficult to navigate. In order to help navigate in the complex venous anatomies, a guide wire has been commonly used. Although an implanter may be able to get the guide wire to the target site, a quadrapolar LV lead generally has a large diameter which makes it difficult for the LV lead to track a guide wire around acute bends.

Although a variety of LV leads, along with methods for implanting such leads, have been developed, there is still a need in the art for developing downsized LV leads and methods of implantation that facilitate pacing or sensing lateral and posterial basal locations of a heart.

BRIEF SUMMARY OF THE INVENTION

Disclosed herein is a left ventricular lead for tracking over a guide wire into a coronary sinus and providing active fixation in, or adjacent to, the coronary sinus. The guide wire is configured for coronary sinus lead implantation and has an outer diameter. In one embodiment, the lead includes a tubular body including a proximal end, a distal end and a central lumen through which the guide wire is extendable. The lead also includes a lead connector end proximally projecting from the proximal end and comprising at least one electrical contact. The lead also includes a fixed helical anchor comprising a wire member having a diameter of between approximately 0.22 mm and approximately 0.27 mm. The wire member distally extends away from the distal end in a helical arrangement including an inner helical coil diameter that is sufficient to allow the guide wire to extend through the fixed helical anchor.

In one embodiment, the inner helical coil diameter is between approximately 0.017 inch and approximately 0.019 inch. The diameter of the wire member is approximately 0.25 mm, and the inner helical coil diameter is approximately 0.018 inch. The tubular body may have a size of approximately 3 F or less.

In one embodiment, the tubular body is configured to provide approximately one-to-one torque transfer between its proximal end and distal end under implantation conditions. For example, the tubular body is configured to provide a torque transfer of at least approximately 65 percent between its proximal end and distal end under implantation conditions. In other words, the torque transfer is such that a 20 degree rotation at the proximal end results in at least approximately 13 degrees of rotation at the distal end under implantation conditions.

In one embodiment, the tubular body includes a polyethylene terephthalate (PET) braided quatra-filer cable helically coiled over a polytetrafluoroethylene (PTFE) liner. The tubular body further includes a reflowed layer of silicone rubber polyurethane co-polymer (SPC) extending over the polytetrafluoroethylene (PTFE) liner and the polyethylene terephthalate (PET) braided quatra-filer cable.

In one embodiment, the wire member comprises a distal tip configured such that, when the guide wire extends through the tubular body and fixed helical anchor, an extreme distal point of the distal tip is positioned and oriented relative to an outer cylindrical surface of the guide wire such that the distal extreme distal point is generally prevented from tissue cutting when the fixed helical anchor is rotated about a longitudinal center axis of the guide wire or the lead is tracked along the guide wire. In such an embodiment, the extreme distal point may be generally tangential with the outer cylindrical surface. The extreme distal point may be generally flush with the outer cylindrical surface.

The wire member may include a most distal coil distally terminating in the extreme distal point of the distal tip and including a radially inner curved boundary and a radially outer curved boundary opposite the radially inner curved boundary. The distal tip proximally may begin on the radially outer curved boundary and distally terminate in the extreme distal point at the radially inner curved boundary. The distal tip may include a bevel including: a proximal border on the radially outer curved boundary; and a distal border on the radially inner curved boundary.

The bevel may include a curved surface or a planar surface between the proximal border and the extreme distal point. The extreme distal point may be defined at least in part by an intersection of the radially inner curved boundary and the bevel.

In one embodiment, the lead further includes a ring shaped electrode on the tubular body and proximal the distal end, at least one of the ring shaped electrode or the fixed helical anchor being in electrical communication with the at least one electrical contact. In one embodiment, the lead is quadrapolar.

In one embodiment, the above-described lead may be part of a system further including the guide wire, wherein the inner helical coil diameter is between approximately 0.002 inch and approximately 0.004 inch larger than the outer diameter of the guide wire. The outer diameter of the guide wire may be between approximately 0.012 inch and approximately 0.018 inch or even between approximately 0.014 inch and approximately 0.016 inch, in one embodiment. The guide wire may include a proximal handle coupled to an end of the guide wire near the proximal end of the tubular body. The tubular body rotates with the guide wire by rotating the proximal handle. In one embodiment, the guide wire includes a metal and has an outer diameter of between approximately 0.015 inch and approximately 0.016 inch, and the inner helical coil diameter is approximately 0.018 inch.

In one embodiment, the above-described lead may be part of a system further including a pulse generator.

Also disclosed herein is a method of implanting a left ventricular lead in tissue of a coronary sinus or an adjacent vascular structure with active fixation In one embodiment, the method includes: negotiating a guide wire through a patient cardiovascular system until a distal end of the guide wire is located in the coronary sinus or the adjacent vascular structure; advancing a left ventricular lead over the guide wire until a fixed helical anchor distally projecting from a distal end of the lead is located in the coronary sinus or the adjacent vascular structure, the engagement of the fixed helical anchor with cardiovascular system tissue being inhibited during the advancement of the lead over the guide wire by the guide wire extending through the fixed helical anchor during the advancement; proximally withdrawing the guide wire from the left ventricular lead an amount sufficient to cause the guide wire to vacate the fixed helical anchor; and rotating the left ventricular lead to cause the vacated fixed helical anchor to screw into the tissue of the coronary sinus or adjacent vascular structure.

With respect to the method disclosed herein, in one embodiment, rotating the left ventricular lead may further include causing the left ventricular lead to rotate with the guide wire or about the guide wire.

With respect to the method disclosed herein, in one embodiment, the fixed helical anchor may include a wire member including a diameter of between approximately 0.22 mm and approximately 0.27 mm, the wire member distally extending away from the distal end in a helical arrangement including an inner helical coil diameter that is sufficient to allow the guide wire to extend through the fixed helical anchor. The inner helical coil diameter may be between approximately 0.017 inch and approximately 0.019 inch. In one embodiment, the diameter of the wire member may be approximately 0.25 mm, and the inner helical coil diameter is approximately 0.018 inch. The tubular body may have a size of approximately 3 F or less.

With respect to the method disclosed herein, in one embodiment, the left ventricular lead may include a tubular body configured to provide approximately one-to-one torque transfer between its proximal end and distal end under implantation conditions. For example, the tubular body may be configured to provide a torque transfer of at least approximately 65 percent between its proximal end and distal end under implantation conditions. In other words, the torque transfer may be such that a 20 degree rotation at the proximal end results in at least approximately 13 degrees of rotation at the distal end under implantation conditions.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

The description will be more fully understood with reference to the following figures, which are presented as various embodiments of the disclosure and should not be construed as a complete recitation of the scope of the disclosure, wherein:

FIG. 3 is an assembled view of the guide wire in the LV lead of FIG. 2.

FIG. 4A is an enlarged view of the helical anchor region of FIG. 3 with another embodiment of the helical coil including fewer number of coils.

FIG. 4B is an enlarged view of the helical screw region of FIG. 3 with an embodiment employing double helical coils.

DETAILED DESCRIPTION

Figure 1:
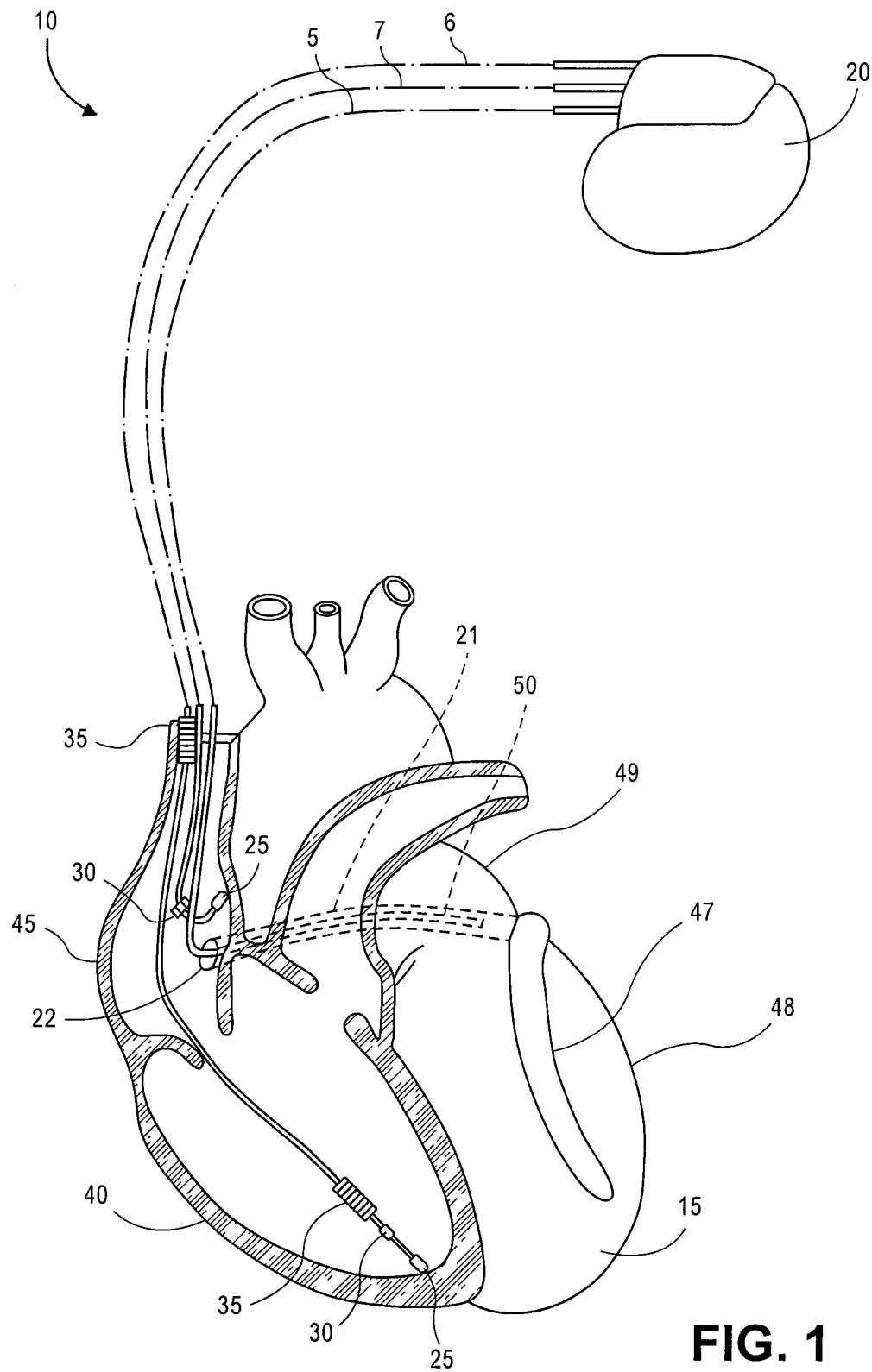
FIG. 1 is a diagrammatic depiction of an electrotherapy system electrically coupled to a patient heart as shown in an anterior view, a distal portion of a LV lead being implanted in the CS.

The present disclosure provides implantable LV leads and methods of implantation that facilitate stimulation of lateral and posterior basal regions of a heart. The LV lead has a small diameter and an active fixation configuration that allows the distal end of the LV lead to be actively fixed at an implantation site in the lateral and posterior basal regions of the heart. The active fixation configuration may be in the form of an active fixation helical arrangement with an internal diameter that closely approximates an outer diameter of a guide wire over which the lead distal end is tracked to the implantation target site, the close tolerance between the diameters of the active fixation arrangement and the guide wire preventing the active fixation arrangement from snagging vasculature or heart tissue premature to the active fixation arrangement being purposely fixed to tissue in the course of the lead being implanted at an implantation target site. The LV lead includes a proximal end that can be connected to a pulse generator (e.g., pacemaker, implantable cardioverter defibrillator (ICD), or etc.). The LV lead also includes electrodes at its distal end to sense electrical signals in the heart tissue and deliver electrical pulses from the pulse generator to the heart tissue of the lateral and posterior basal regions in the heart.

The present disclosure provides a downsized LV lead (e.g. 3 F LV lead) with an active fixation configuration at its distal end. By using the active fixation to attach the LV lead to the tissue at a target implant site, the LV lead can be assured to remain at the target implant site. The active fixation can allow the LV lead to have a reduced size as compared to the size of passive fixation LV leads. Specifically, passive fixation may require a relatively stiff LV lead for stabilization at a target implant site. Such lead stiffness may not be obtained for a LV lead with reduced diameter. For example, to stabilize a LV lead in remaining at the target implant site, passive fixation may use a known "S-shaped" structure. As the LV lead is downsized, the stiffness of the LV lead may decrease with the fourth power of the radius of the LV lead. Therefore, the lateral forces of the "S-shaped" structure exerted against the vessel walls of a vein by a downsized 3 F lead are dramatically lower than the forces exerted by a larger 5 F lead. Also, it may not be desirable to add a stiffening wire in the lead body because the stiffening wire may take more space and may present a risk of perforation should the lead body fail. The active fixation may also allow the LV lead to be positioned anywhere in the heart, unlike passive fixation as made possible via an "S-shaped" lead body structure or as made possible via passive fixation tines.

The LV lead may include an elongated tubular body having a distal end and a proximal end. The LV lead may also include an active fixation configuration in the form of a hollow helical screw or helical anchor fixedly attached to the distal end of the tubular body for active fixation to the coronary sinus or adjacent vascular structures or heart tissue. The LV lead may also include a lead connector attached to the proximal end of the tubular body for connecting to a pulse generator.

As already noted, on account of the configuration of the helical anchor relative to the configuration of the guide wire over which the lead is tracked through the patient, the helical anchor may be protected from inadvertently snagging patient tissue as the lead is tracked over the guide wire to reach to the target implant site. The tubular body of the LV lead can be turned or rotated with the guide wire or around the guide wire to allow the helical anchor to engage the tissue. The guide wire may include a proximal handle at a proximal end such that the guide wire may be turned by using the proximal handle and to cause the tubular body of the LV lead to rotate with the guide wire.

A general, non-limiting discussion is now provided regarding some of the features and deployment characteristics common among the various lead and implantation embodiments disclosed herein. FIG. 1 is a diagrammatic depiction of an electrotherapy system 10 electrically coupled to a patient heart 15 as shown in an anterior view. As shown in FIG. 1, the system 10 includes an implantable pulse generator 20 (e.g., pacemaker, implantable cardioverter defibrillator (ICD), or etc.) and one or more (e.g., three) implantable medical leads 5, 6, 7 electrically coupling the patient heart 15 to the pulse generator 20. While the following discussion will focus on the configuration and implantation of the left ventricular (LV) lead 5 extending into the coronary sinus (CS) 21 via the coronary sinus ostium (OS) 22, it should be remembered that the system 10 may employ only the LV lead 5 or the LV lead 5 in conjunction with other leads, such as, for example, a right ventricular (RV) lead 6 and/or right atrial (RA) lead 7. The RV and RA leads 6, 7 may employ pacing electrodes 25, sensing electrodes 30 and shock coils 35 as known in the art to respectively provide electrical stimulation to the right ventricle 40 and right atrium 45 of the heart 15.

As can be understood from FIG. 1, which shows an anterior view of the patient heart 15, the CS 21 extends generally from the OS 22 and, further, posterior to anterior until transitioning into the great cardiac vein or coronary vein 47, which then extends in a generally inferior direction along the anterior region of the left ventricle (LV) 48. In extending generally posterior to anterior from the OS 22 until transitioning into the great cardiac vein 47, the CS 21 is inferior to the left atrium (LA) 49 and superior to the LV 48.

As indicated in FIG. 1, in most embodiments of the LV lead 5 disclosed herein, the distal portion 50 of the LV lead 5 may extend into the great cardiac vein 47 and be implanted in vein 47. The distal portion 50 may also be implanted in the CS 21 or vein branches extending off of the CS 21. The distal portion 50 of each embodiment of the LV lead 5 disclosed herein is configured to facilitate implanting in the CS 21 or vein 47, more particularly, in the lateral and posterior basal region of the heart. Because of its active fixation capability and the smallness of its active fixation anchor, as described below, the distal end of the LV lead 5 can be actively affixed to the LV heart wall or the vessel wall of the CS 21, great coronary vein 47 or other related vasculature walls with little risk from the active fixation.

Figure 2:
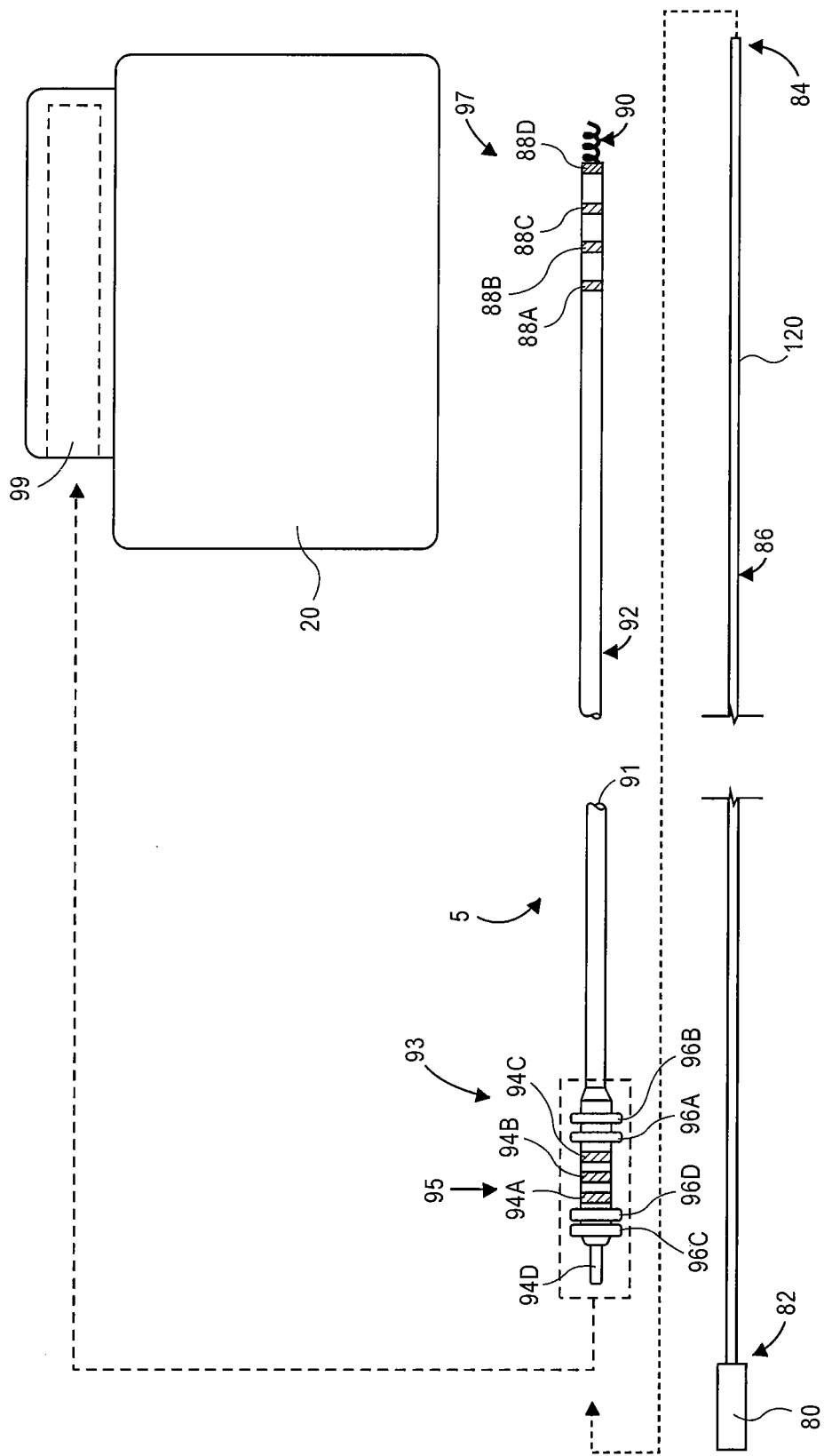
FIG. 2 illustrates a LV lead that can be attached to a pulse generator (e.g., pacemaker, implantable cardioverter defibrillator (ICD), or etc.) and be delivered to an implantation target sit via the use of a guide wire in accordance with embodiments of the present disclosure.

FIG. 2 illustrates a LV lead 5 that can be attached to a pulse generator 20 and be delivered to an implantation target sit via the use of a guide wire in accordance with embodiments of the present disclosure. As shown, a LV lead 5 includes an elongated tubular body 92 that includes a proximal end 93, a distal end 97 opposite to the proximal end 93, and an elongated central lumen 91 extending between the proximal end 93 and the distal end 97. The central lumen 91 may be generally in a cylindrical shape. The central lumen 91 allows a guide wire 86 to pass through from the proximal end 93 to the distal end 97.

The LV lead 5 also includes a hollow helical anchor 90 fixedly attached to the distal end 97 of the tubular body 92. The helical anchor 90 may be engaged with the heart wall or vascular tissue and provide active fixation to remain at a target or desired implant site associated with LV implantation. More details of the helical anchor 90 will be illustrated in FIGS. 3-6 and described later.

The LV lead 5 may also include four ring shaped electrodes 88A-D outside the tubular body 92 near the distal end and are generally flush with the outer surface of the tubular body 92. The ring shaped electrodes 88A-D may be spaced apart from each other. The distance between the electrodes may vary. The three electrodes 88A-C are near the distal end 97 of the tubular body 92 while ring shaped electrode 88D may be positioned at the distal end 97 of the tubular body 92 and is electrically connected to the helical anchor 90. Each ring electrode 88A-D and the helical anchor 90 may be formed of a biocompatible electrically conductive metal (e.g., stainless steel, gold platinum, platinum-iridium alloy, etc.) and can server as an electrode for pacing (e.g., delivering stimulation to the heart) and/or sensing electrical activities from the heart.

A guide wire 86 may be used for assisting the LV lead to reach a target implant site and to inhibit the engagement of the helical anchor with cardiovascular system tissue during the advancement of the LV lead to the target implant site. The guide wire 86 may have a distal end 84, a proximal end 82, and an elongated body having an outer surface 120 extending between the distal end 84 and the proximal end. The guide wire may be in a general cylindrical shape. A proximal handle 80 may be connected to the proximal end 82 of the guide wire to assist with rotating the guide wire by hand. The guide wire 86 may be configured to be inserted into the LV lead 5 from a lead connector end 95 of the proximal end 93 of the tubular body 92 and to pass through the central lumen 91 to extend beyond the distal end 97 of the tubular body 92, thereby passing through the helical anchor 90 to extend beyond the most distant coil of the helical anchor 90, as reflected in FIG. 3 discussed below.

The LV lead 5 may further include the lead connector end 95 proximally projecting from the proximal end 93 of the tubular body 92. The lead connector end 95 may include ring contacts 94A-C that are positioned between inner seals 96A and 96D. The inner seals 96A and 96D may be used to isolate the ring contacts from any body fluids. Additional outer seals 96B and 96C may be positioned at a further distance from the ring contacts 94A-C than the inner seals 96A and 96D to further prevent the body fluids from entering the space between the inner seals 96A and 96D. These seals may be formed of insulating materials, such as biocompatible polymers or rubbers. The lead connector end 95 may also include a hollow pin contact 94D proximally projecting from the outer seal 96C and through which the guide wire may be inserted through the connector end 95 and into the central lumen 91 of the lead body 92. These contacts 94A-D are in electrical communication with the respective ring shaped electrodes 88A-D near the distal end 97. For example, these contacts 94A-D are electrically coupled to respective conductors (e.g., coiled conductors, or cable or stranded conductors as known in the art) that extend through the lead from the contacts 94A-D to the ring shaped electrodes 88A-D.

The lead connector end 95 is configured to be inserted into a receptacle 99 of the pulse generator 20 to so the contacts 94A-D can electrically couple with the circuitry of the pulse generator 20, thereby allowing the pulse generator to sense cardiac electrical signals and administer electrotherapy via the lead. The lead connector end 95 includes a hollow central portion configured to allow the guide wire 86 to pass through the lead connector end and into the lumen of the lead body, as already mentioned above. The lead connector end 95 is fixedly attached to the tubular body 92 near the proximal end 93 of the tubular body 92.

Quadrapolar electrodes are commonly used in LV leads. The quadrapolar electrodes may be used to sense signals from the heart or deliver electrical stimulation to pace the heart by using an electrical pulse generator or pace maker 20 as shown in FIG. 2. In some embodiments, the electrodes may be ring shaped, such as shown in FIG. 2, or other shapes. The ring shaped electrodes may be coaxial with the tubular body 92. The most distal ring shaped electrode 88D at the distal end of the tubular body 92 may be connected to the helical screw 90, which may provide therapy to the heart along with the most distal ring shaped electrode. The electrical signals may along the conductors of the lead body between the electrodes 88A-D and the pulse generator 20, and vice versa, in the course of electrotherapy being administered to the cardiac tissue of the LV. While, a quadrapolar electrode arrangement is depicted in the figures, it will be appreciated by those skilled in the art that the electrodes may alternatively be of a unipolar, bipolar, or multipolar electrode arrangement.

FIG. 3 is an assembled view of the guide wire 86 in the LV lead 5 of FIG. 2. As shown, system 300 includes the guide wire 86 inserted into the tubular body 92 of the LV lead 5 from the lead connector end 95. The guide wire 86 passes through the lead connector end 95, the central lumen 91 of the tubular body 92, and also the helical anchor 90, the guide wire extending beyond the most distant coil 85 of helical anchor 90. This guide wire 86 extending beyond the helical anchor may help protect the helical anchor 90 from engaging patient cardiovascular tissue during the advancement of the LV lead to reach a target implant site. In other words, the helical screw or anchor 90 is protected from snagging the patient cardiovascular tissue during tracking of the lead distal end 97 through the vasculature of the patient by using the guide wire 86 in a manner such that the guide wire 86 passes through the helical screw 90 in close tolerances and extends beyond the distal end 97 of the LV lead 5 and the helical anchor 90. As a result, the guide wire 86 interferes with the helical anchor 90 engaging the cardiovascular tissue as the LV lead 5 is advanced.

The helical anchor 90 includes a few turns of the coil 85 including the most distant turn that terminates. The coil is arranged in a helical configuration around a longitudinal axis 95 of the tubular body 92. As discussed in greater detail below, the coil 85 has an inner diameter that is only slightly larger than an outer diameter of the guide wire 86 such that the guide wire prevents the helical anchor from engaging or damaging cardiac tissue in the process of the lead being tracked over the guide wire in the course of the lead being implanted in the patient. Once the guide wire is withdrawn from the confines of the helical anchor and the helical anchor is placed against cardiac or other patient tissue, the lead may be rotated around its longitudinal axis 95 to cause the helical anchor 90 to rotate around the longitudinal axis 95 and screw into the tissue.

An enlarged view of the helical anchor 90 and distal end of the lead is shown in FIGS. 4A and 4B, but with different embodiments of the helical anchor 90. As shown in FIG. 4A, the helical anchor may have one full turn of the coil 85 instead of a few turns of the coil 85 as shown in FIG. 3. Similar to the helical anchor illustrated in FIG. 3, the helical anchor of FIG. 4A may be in the form of a single helical coil arrangement formed from a single helically wound member (e.g., a helically wound wire). The most distal ring shaped electrode 88D may be positioned on the tubular body 92 near the distal end 97 of the tubular body 92, and may be electrically connected to the helical anchor 90. The ring shaped electrode 88D may be generally flush with the tubular body 92.

As shown in FIG. 4B, the helical anchor 90 may include double helical coils 87 and 85 that are wound in opposite directions and may be 180° out of phase. Both helical coils 87 and 85 may be electrically connected to the ring shaped electrode 88D which is on the tubular body 92. The double helical coils may provide better engagement with the tissue than a single helical coil. It will be appreciated by those skilled in the art that the helical anchor may vary in coil configuration or shape. In some embodiments, the helical anchor may not serve as an electrode, but instead solely functions as a fixation device.

The lead may be caused to rotate about its longitudinal axis via rotation of the guide wire 86 extending through the lead. The lead may be caused to rotate about its longitudinal axis by a rotational force being exerted on the proximal end of the lead. The lead tubular body 92 is configured to provide approximately one-to-one torque transfer between the proximal end 93 and distal end 97 of the tubular body 92 under implantation conditions. For example, in some embodiments, the torque transfer may be at least approximately 65 percent between its proximal end and distal end under implantation conditions. For example, the torque transfer may allow a 20 degree rotation at the proximal end resulting in at least approximately 13 degrees of rotation at the distal end under implantation conditions.

The tubular body 92 may have a size of approximately 3 F or less such that the LV lead can be small enough used in patients with very small veins. This size is significantly smaller than conventional 5 F or 6 F LV lead.

In one embodiment, to facilitate the above-described torque transfer characteristics, the tubular body 92 may be formed of a biocompatible polymer which has relatively high stiffness such that the tubular body can provide one-to-one torque transfer or at least 65 percent torque transfer, as discussed above. The polymers may include, but are not limited to, a polyethylene terephthalate (PET) braided quatra-filer cable helically coiled over a polytetrafluoroethylene (PTFE) liner. In a particular embodiment, the tubular body may be formed of a reflowed layer of silicone rubber polyurethane co-polymer (SPC) extending over the polytetrafluoroethylene (PTFE) liner and the polyethylene terephthalate (PET) braided quatra-filer cable. The tubular body 92 may be constructed by using DACRON® braided quatra-filer coiled cable over a TEFLON® liner, such that the LV lead 5 can transfer torque from a proximal end to the distal end as described above. For further discussion of lead body configurations useful in achieving the above-described torque transfer performance, see U.S. patent application Ser. No. 14/080,676, which was filed Nov. 14, 2014, is entitled "MRI Compatible Implantable Lead" and claims priority to U.S. Application No. 61/784,985, which was filed Mar. 14, 2013, these applications being incorporated by reference herein in their entireties.

Referring to FIG. 3 again, the tubular body 92 is coaxial with the guide wire 86 prior to being implanted into a patient cardiovascular system. The tubular body 92 and the guide wire 86 may have interference when implanted such that the tubular body 92 may be caused to rotate with the guide wire 86 or around the guide wire 86. When the guide wire 86 is rotated by the proximal handle 80, the tubular body 92 may rotate with the guide wire 86 to transfer the torque from the proximal end 82 to the helical anchor 90 that is fixedly attached to the distal end of the tubular body 92. With the transferred torque, the helical screw 90 may rotate to attach to the tissue, such as coronary sinus 21. To verify if the helical screw 90 is fixedly attached to the tissue, an implanter may gently tug on the LV lead 5 to verify the active fixation. Alternatively, instead of employing the guide wire to bring about rotation of the lead body, the lead connector end 95 may be grasped and rotated to bring about the rotation of the lead body, and by extension, the helical anchor. Alternatively, the lead and guide wire may both be grasped to apply rotation to the assembled devices as a whole or individually in a vice versa manner to bring about the rotation of the lead body used to screw the helical anchor into the tissue.

The helical screw 90 and the guide wire 86 may be configured to have a tolerance to allow the guide wire 86 to easily extend through the helical screw 90 and to be smoothly pulled back to vacate the helical screw 90 without resistance or friction. In some embodiments, the inner diameter of one full turn of the helical coil, also referred to as the inner helical coil diameter, may be between approximately 0.002 inch and approximately 0.004 inch larger than the outer diameter of the guide wire. The outer diameter of the guide wire 86 may be between approximately 0.015 inch and approximately 0.016 inch. The inner helical coil diameter may be between approximately 0.017 inch and approximately 0.019 inch. In a particular embodiment, the inner helical coil diameter may be approximately 0.018 inch. The helical screw 90 may be formed of biocompatible metal or metal alloys, such as platinum, platinum iridium alloy, MP35N, or stainless steel, and may act as an anchor electrode.

Figure 5:
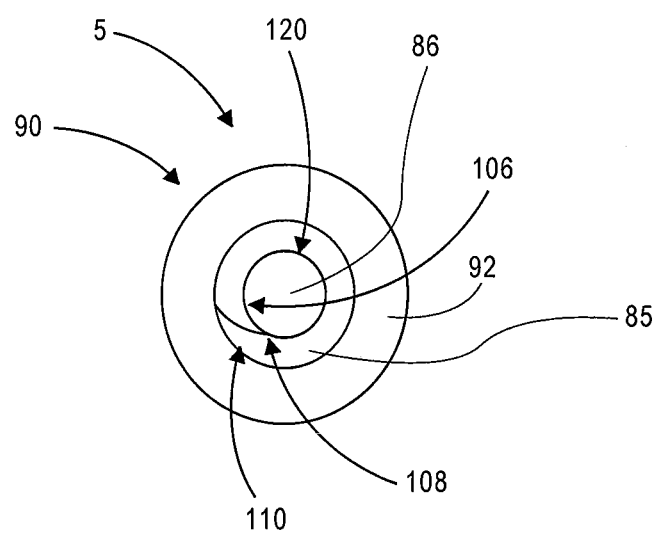
FIG. 5 is an elevation view of the lead distal end as viewed in the direction indicated by arrows 4-4 in FIG. 4A.
Figure 6:
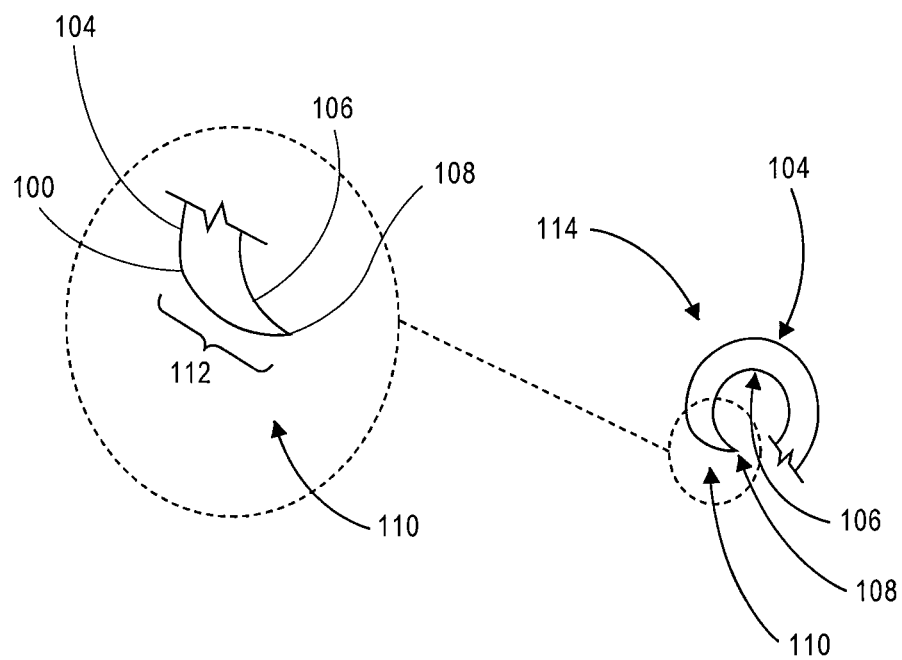
FIG. 6 is the same view as FIG. 5, except showing only the most distal end termination of the helical anchor for clarity purposes.

For a detailed discussion of the structural relationship between the guide wire 86 and the helical anchor 90 in the vicinity of the tip 110 of the helical anchor 90, reference is now made to FIGS. 5 and 6, wherein FIG. 5 is an elevation view of the lead distal end as viewed in the direction indicated by arrows 4-4 in FIG. 4A, and FIG. 6 is the same view as FIG. 5, except showing only the most distal end termination of the helical anchor 90 for clarity purposes. As illustrated in FIGS. 5 and 6, the most distal turn of the coil 85 of the helical anchor 90 includes a radially inner curved boundary 106 and a radially outer curved boundary 104 opposite the radially inner curved boundary 106. The most distal turn of the coil 85 of the helical anchor 90 distally terminates in the tissue penetrating tip 110.

As best understood from the enlarged view of the tip 110 depicted in FIG. 6, the tip 110 proximally begins on the radially outer curved boundary 104 and distally terminates in a point 108 at the radially inner curved boundary 106, the point 108 forming the extreme distal termination of the tissue penetrating tip 110. The tip 110 can be seen to include a grind, taper surface or bevel 112 that has a proximal border 100 on the radially outer curved boundary 104 and a distal border 108 in the form of sharp point on the radially inner curved boundary 106. In one embodiment, the bevel 112 may have a curved surface between the proximal border 100 and the point 108. In other embodiments, the bevel 112 may have a straight, flat or planar surface between the proximal border 100 and the point 108. The point 108 is defined at least in part by an intersection of the radially inner curved boundary 106 and the bevel 112.

As can be understood from FIGS. 4A and 5, the coil or wire member 85 of the helical anchor 90 includes a distal tip 110 which is configured such that, when the guide wire 86 extends through the tubular body 92 and the fixed helical anchor 90, the radially inner curved boundary 106 is immediately adjacent the outer cylindrical surface 120 of the guide wire, and the extreme distal point 108 of the tip 110 is positioned immediately next to and oriented towards the outer cylindrical surface 120 of the guide wire 86. These arrangements help prevent the tip 110 from cutting or otherwise engaging tissue when guide wire extends through the coils of the helical anchor and the helical anchor 90 is rotated about the longitudinal center axis 95 of the guide wire 86 or the LV lead 5 which is tracked along the guide wire 86. To avoid cutting the tissue during advancement of the LV lead 5 over the guide wire 86, the distal tip 110 of the helical anchor is generally tangential with the outer cylindrical surface 120 of the guide wire 86. Also, the distal tip 110 is generally flush with the outer cylindrical surface 120 of the guide wire 86 to avoid the cutting during the lead advancement.

Figure 7:
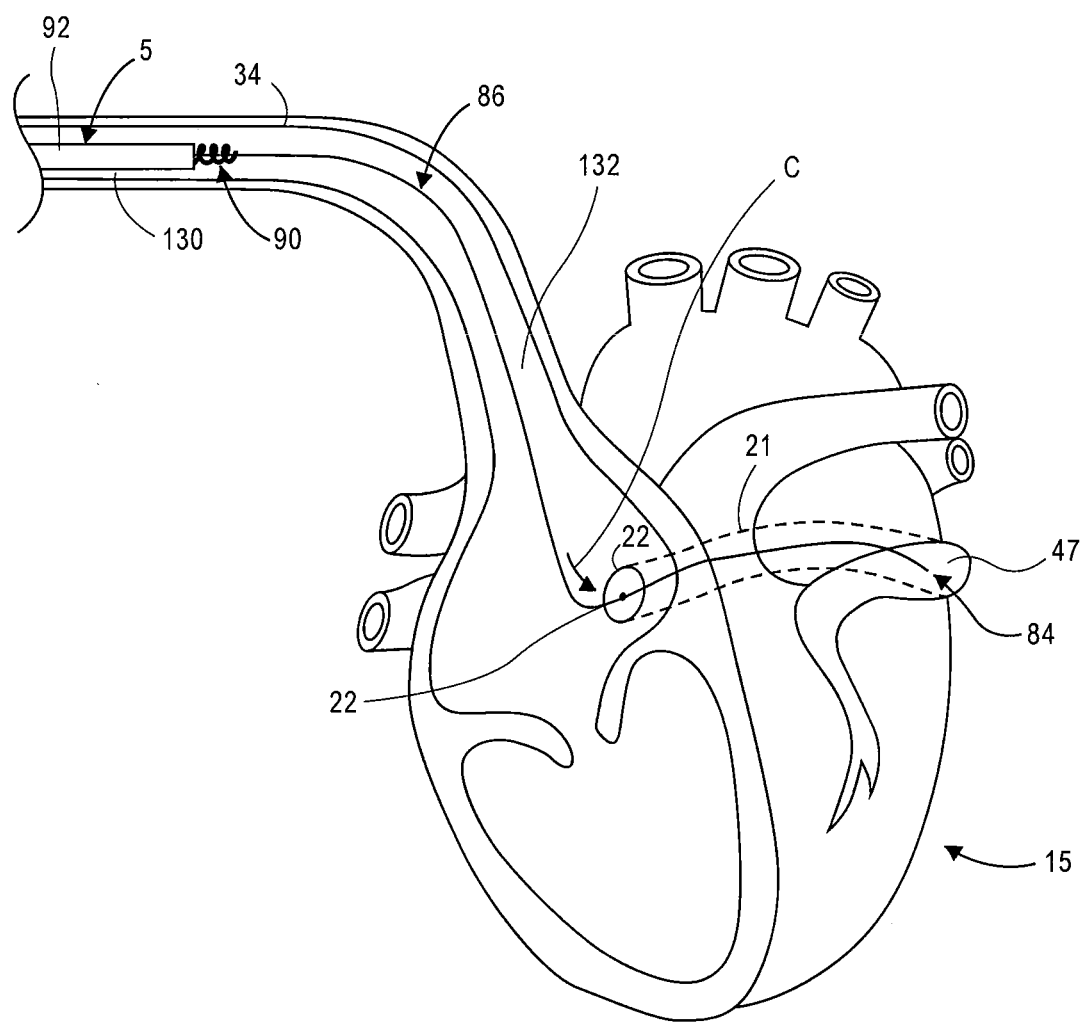
FIG. 7 is a schematic depiction of the medical lead being guided along a guide wire through a subclavian vein to a left side of a heart in accordance with embodiments of the present disclosure.

FIG. 7 is a schematic depiction of the medical lead 5 being guided along the guide wire 86 through a subclavian vein 130 to a left side of a heart 15. As illustrated in FIG. 7, the distal end 84 of the guide wire 86 is advanced ahead of the lead 5 through the superior vena cava (SVC) 132 and into the right atrium region 134. The guide wire 86 is further advanced ahead of LV lead 5 into the coronary sinus (CS) 21 via the coronary sinus ostium (OS) 22 via, as indicated by arrow C. On account of the configuration of the helical anchor tip, as described above, and, as also described above, the complementary configurations of the guide wire and helical anchor and the way in which they interact to prevent the helical anchor point 108 from engaging tissue when the guide wire extends through the coils of the helical anchor, the helical anchor can be exposed as the lead tracks along the guide wire from the SVC 132 and into the CS 21, and the helical anchor point 108 will not catch or snag on cardiac or vascular structures along the way to the implant site in the CS 21 or coronary vein 47. While the lead 5 is being guided along guide wire 86, the lead 5 itself may also be rotated to further prevent the helical anchor point 108 from catching or snagging. For example, if the helical anchor point 108 requires clockwise rotation for fixation at an implant site, counter-clockwise rotation of the lead 5 may reduce the likelihood of catching or snagging.

During a LV lead implantation procedure, which may be visualized via X-ray fluoroscopy, the distal end of the LV lead may be implanted at a target implant site in the coronary sinus 21 or adjacent vascular structure. To deliver the lead distal end to the target implant site, the guide wire 86 may be negotiated through the patient cardiovascular system until the distal end 84 of the guide wire 86 reaches the target implant site. The LV lead 5 may be then advanced over the guide wire 86 until the helical anchor 90 is located in the coronary sinus 21 or the adjacent vascular structure, such as, for example, the coronary vein 47. Then, the guide wire 86 may be proximally withdrawn from the LV lead 5 sufficiently to vacate the helical anchor 90. The proximal end 93 of the LV lead 5 may be rotated to cause the vacated fixed helical anchor 5 to screw into the tissue at the target implant site. The proximal end 93 of the LV lead 5 may be rotated by causing the LV lead to rotate with the guide wire 86 or about the guide wire. For example, the proximal end 82 of the guide wire 86 may be rotated by using the proximal handle 80 to cause the LV lead to rotate with the guide wire, such that the vacated helical anchor can screw into the coronary sinus 21. Alternatively, the distal end of the lead may have a rotational force directly applied to it to cause the lead body to rotate about its longitudinal axis, thereby providing the rotation that causes the helical anchor body to screw into the tissue.

The size and gauge of the active fixation anchor 90 disclosed herein is very small and the process of active fixation in the vein will not result in blood leakage as its resulting very small hole in the vein wall will be sealed off by a platelet plug that readily forms to fill the small hole, thereby preventing any bleeding and working to maintain hemostasis. For this reason, the diameter of the wire used to form the coils of the helical anchor 90 disclosed herein may be very small, ranging between approximately 0.22 mm and approximately 0.27 mm such that the helical anchor may pierce a very small hole or perforation when placed in the vein during active fixation. In a particular embodiment, the wire forming the coils of the helical anchor 90 disclosed herein may have a diameter on the order of 0.25 mm which is about the size of a 31 gauge hypodermic needle.

The downsized LV lead provides many benefits including, for example, being able to implant a lead in a patient with small veins or complex venous anatomies, reducing implantation operation time, and improved tracking as compared to larger diameter quadrapolar leads. The benefits of using the downsized LV lead may also include precisely placing the LV lead at targeted implant sites, which may improve patient outcomes. For example, the basal LV pacing may have better results by precisely placing the LV leads at targeted implant sites. The downsized LV lead may be used to assist implanters in rapidly positioning the LV lead or guide wire at targeted implant sites and thus help implant times and reduce the exposure to X-rays.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A left ventricular lead for tracking over a guide wire into a coronary sinus and providing active fixation in, or adjacent to, the coronary sinus, the guide wire being configured for coronary sinus lead implantation and having an outer diameter defined by an outer cylindrical surface, the lead comprising:

a tubular body comprising a proximal end, a distal end and a central lumen through which the guide wire is extendable;

a lead connector end proximally projecting from the proximal end and comprising at least one electrical contact; and a fixed helical anchor comprising a wire member having a diameter of between approximately 0.22 mm and approximately 0.27 mm, the wire member distally extending away from the distal end in a helical arrangement including an inner helical coil diameter defined by a radially inner curved boundary, the inner coil diameter having a size relationship with the outer diameter of the guide wire with the inner coil diameter being larger than the outer diameter of the guide wire within a small range, the size relationship positioning the radially inner curved boundary of the wire member immediately adjacent the outer cylindrical surface of the guide wire when the guide wire extends through the fixed helical anchor.

2. The lead of claim 1, wherein the inner helical coil diameter is between approximately 0.017 inch and approximately 0.019 inch.

3. The lead of claim 2, wherein the diameter of the wire member is approximately 0.25 mm, and the inner helical coil diameter is approximately 0.018 inch.

4. The lead of claim 1, wherein the tubular body has a size of approximately 3 F or less.

5. The lead of claim 4, wherein the tubular body is configured to provide approximately one-to-one torque transfer between its proximal end and distal end under implantation conditions.

6. The lead of claim 4, wherein the tubular body is configured to provide a torque transfer of at least approximately 65 percent between its proximal end and distal end under implantation conditions.

7. The lead of claim 6, wherein the torque transfer is such that a 28 degree rotation at the proximal end results in at least approximately 13 degrees of rotation at the distal end under implantation conditions.

8. The lead of claim 6, wherein the tubular body comprises a polyethylene terephthalate (PET) braided quatra-filer cable helically coiled over a polytetrafluoroethylene (PTFE) liner.

9. The lead of claim 8, wherein the tubular body further comprises a reflowed layer of silicone rubber polyurethane co-polymer (SPC) extending over the polytetrafluoroethylene (PTFE) liner and the polyethylene terephthalate (PET) braided quatra-filer cable.

10. The lead of claim 1, wherein the wire member comprises a distal tip configured such that, when the guide wire extends through the tubular body and fixed helical anchor, an extreme distal point of the distal tip is positioned and oriented relative to an outer cylindrical surface of the guide wire such that the distal extreme distal point is generally prevented from tissue cutting when the fixed helical anchor is rotated about a longitudinal center axis of the guide wire or the lead is tracked along the guide wire.

11. The lead of claim 10, wherein the extreme distal point is generally tangential with the outer cylindrical surface.

12. The lead of claim 10, wherein the extreme distal point is generally flush with the outer cylindrical surface.

13. The lead of claim 10, wherein the wire member includes a most distal coil distally terminating in the extreme distal point of the distal tip and including a radially inner curved boundary and a radially outer curved boundary opposite the radially inner curved boundary.

14. The lead of claim 13, wherein the distal tip proximally begins on the radially outer curved boundary and distally terminates in the extreme distal point at the radially inner curved boundary.

15. The lead of claim 13, wherein the distal tip includes a bevel including: a proximal border on the radially outer curved boundary; and a distal border on the radially inner curved boundary.

16. The lead of claim 15, wherein the bevel includes a curved surface or a planar surface between the proximal border and the extreme distal point.

17. The lead of claim 15, wherein the extreme distal point is defined at least in part by an intersection of the radially inner curved boundary and the bevel.

18. The lead of claim 1, further comprising a ring shaped electrode on the tubular body and proximal the distal end, at least one of the ring shaped electrode or the fixed helical anchor being in electrical communication with the at least one electrical contact.

19. The lead of claim 1, wherein the lead is quadrapolar.

20. A method of implanting a left ventricular lead in tissue of a coronary sinus or an adjacent vascular structure with active fixation, the method comprising:
  negotiating a guide wire through a Patient cardiovascular system until a distal end of the guide wire is located in the coronary sinus or the adjacent vascular structure, the guide wire having an outer diameter defined by an outer cylindrical surface;
  advancing a left ventricular lead over the guide wire until a fixed helical anchor distally projecting from a distal end of the lead is located in the coronary sinus or the adjacent vascular structure, the fixed helical anchor having an inner helical coil diameter defined by a radially inner curved boundary, the inner coil diameter having a size relationship with the outer diameter of the guide wire with the inner coil diameter being larger than the outer diameter of the guide wire within a small range, the size relationship positioning the radially inner curved boundary of the fixed helical anchor immediately adjacent the outer cylindrical surface of the guide wire when the guide wire extends through the fixed helical anchor during the advancement, the engagement of the fixed helical anchor with cardiovascular system tissue being inhibited during the advancement of the lead over the guide wire by the guide wire extending through the fixed helical anchor during the advancement;
  proximally withdrawing the guide wire from the left ventricular lead an amount sufficient to cause the guide wire to vacate the fixed helical anchor; and
  rotating the left ventricular lead to cause the vacated fixed helical anchor to screw into the tissue of the coronary sinus or adjacent vascular structure.

\* \* \* \* \*